US006718007B1

(12) United States Patent
James

(10) Patent No.: US 6,718,007 B1
(45) Date of Patent: Apr. 6, 2004

(54) USING HAIR TO SCREEN FOR BREAST CANCER

(75) Inventor: Veronica Jean James, Kenthurst (AU)

(73) Assignee: Fiberscan PTY Ltd., Queensland (AU)

( * ) Notice: Subject to any disclaimer, the term of this patent is extended or adjusted under 35 U.S.C. 154(b) by 0 days.

(21) Appl. No.: 09/857,665

(22) PCT Filed: Dec. 10, 1999

(86) PCT No.: PCT/AU99/01100

§ 371 (c)(1),
(2), (4) Date: Sep. 6, 2001

(87) PCT Pub. No.: WO00/34774

PCT Pub. Date: Jun. 15, 2000

(30) Foreign Application Priority Data

Dec. 10, 1998 (AU) .............................................. PP 7646
Nov. 2, 1999 (AU) ........................................... PQ 3813

(51) Int. Cl.$^7$ ............................................. G01N 23/20
(52) U.S. Cl. .............................. 378/70; 378/71; 378/86; 378/88
(58) Field of Search .............................. 378/70, 71, 86, 378/88, 89, 90, 79; 209/589

(56) References Cited

U.S. PATENT DOCUMENTS 5,717,733 A * 2/1998 Kurbatov et al. .............. 378/71
6,316,234 B1 * 11/2001 Bova ........................ 435/173.7

OTHER PUBLICATIONS

James, V.J. et al. "Using Hair to Screen for Breast Cancer" Nature, vol. 398, pp. 33–34 (1999).*
Briki. et al. "Breast Cancer diagnosis using Hair" Nature, vol. 400, (Jul. 15, 1999).*
James, V.J. "Experimental Procedure for Hair Diffraction Studies", http://www.ansto.gov.au/natfac/asrp9.html, (Jun. 1999).*
Chengyu, Z., et al "Analysis of Trace Elmts in Scalp Hair of Healthy People, Breast Cancer and Hyperplasia Patients with XRF Method." Datebase Biosis online! Biosciences Info Service, Phila., PA "1993" Database access No. XP–002207802.
Kolmogorov, Y, et al "Analysis of trace elements in scalp hair of healthy people, hyperplasia and breast cancer patients with XRF method" Nuclear Instruments and Methods in Physics Research A 448 (2000) "457–460".
James, V.J. et al. "Using Hair to Screen for Breast Cancer" Nature, vol. 398, pp. 33–34, (1999).
James, V.J. et al. "Changes in the Molecular Structure of Hair in Insulin–Dependent Diabetes" Biochemical and Biophysical Research Communications, vol. 233, pp. 76–80, (1997).
Derwent Abstract Accession No. 96–209368/21, WO 9610648, Apr. 11, 1996.
Derwent Abstract Accession No. 91–031474/05, FR 2647906, Dec. 7, 1990.

* cited by examiner

Primary Examiner—Craig E. Church
Assistant Examiner—Jurie Yun
(74) Attorney, Agent, or Firm—Ladas & Parry

(57) ABSTRACT

A method for detecting the presence of a gene responsible for a pathological state; or the pathological state itself in a patient comprising exposing at least one hair from the patient to fibre X-ray diffraction and detecting changes in the ultrastructure of the hair. An instrument (1) for detecting the presence of a gene responsible for a pathological state; or de pathological state itself, using a hair sample, comprising: an X-ray source (2) producing a beam of X-ray radiation; a sample stage for positioning said hair (3) sample within said beam; a detector to detect the scanering of said X-ray beam caused by said hair sample; and a display means (9) associated with said detector for displaying the output thereof (9a, 9b, 9c and 9d); whereby patterns of output related to the presence of said gene or said pathological state are displayed for interpretation.

18 Claims, 9 Drawing Sheets

USING HAIR TO SCREEN FOR BREAST CANCER

FIELD OF THE INVENTION

The present invention relates to a method of testing the presence of a gene responsible for a pathological state, or the pathological state itself, in biological material in which the molecules are regularly arrayed. Specifically, the present invention relates to analysing hair for detecting the presence of BRCA I gene, the presence of breast cancer per se, the presence of prostate cancer and a confirmatory diagnosis for Alzheimer's disease.

BACKGROUND OF INVENTION

Breast cancer is still a major cause of death in women in Australia. It has been established that approximately 14% of Australian women will have it during their life-time. However, if the cancer is diagnosed early enough, while it is still contained within the breast, there is approximately 98% chance of obtaining a total cure. An early low-cost diagnostic tool would be a major break-through in this area of medicine.

The genes responsible for familial breast cancer have already been located and clinics are being formed to closely monitor those whose family members have been shown to test positive to the gene. These tests however take weeks to complete, are extremely costly and cannot therefore be extended to all women and are at present limited to the high risk group of persons whose mothers had breast cancer.

At present a very expensive and time consuming test is used to determine the carriers of genes, such as breast cancer genes.

The technique of this invention provides a relatively low cost, approximately 1 minute alternative test. It also offers a possible mass screening technique for example, for breast cancer per se with easy access to sample collection and handling. Such a test may replace mammography which is not only expensive, requires attendance at various locations and from the woman's point of view is quite painful but also is not 100% reliable and in some cases very difficult to interpret.

SUMMARY OF INVENTION

Considered at the microscopic level, a single hair consists of a core (the medulla) surrounded by an intermediate layer (the cortex) and then by a thin outer envelope (the cuticle). The cortex can be considered as a continuous network of α-keratin fibrils arranged parallel to the length of the hair and held together by a cell membrane complex. During keratinisation in the follicle each individual cortical cell is wrapped in a plasma membrane, which is basically a biomolecular layer of phospholipids, which acts as the adhesive between neighbouring cells. Such a regular array is ideally suited to fibre x-ray diffraction analysis, and the ultrastructure of human hair has been previously determined from high-intensity synchrotron radiation scattering data combined with results from physical swelling and stretching experiments. These data show the major components of the cortex to be hexagonal arrays of α-keratin fibrils comprising the intermediate filaments (IFs). The fundamental unit of the IF is the double helical α-keratin chain. Two of these coils together to form a tightly bound tetramer. Eight of the tetramers then wind in a slow helix to form the outer layer of the IF. The eight tetrameric units are staggered so that the commencement of the seventh is directly above the first and the whole assembly is tilted at an angle of 7°, thus providing the six linkages in one complete turn around the IF to form an hexagonal array. The α-helical units of the IFs with their shorter linker unit consist of around 311–312 residues, which corresponds to the 47.0 nm repeat in the fibre direction. The axial repeat of the linkage attachment points, at 62.7 nm in the fibre direction, correspond to the non-helical tail repeats along the inclined tetrameric units. A typical x-ray diffraction pattern obtained from normal subjects between the ages of 4 and 80 is given in FIG. 2, that from persons with breast cancer is given in FIG. 3.

Low angle fibre X-ray diffraction along with appropriate analysis will yield the molecular structure of any material in which there is a regular array of molecules. Hair is such a material, characterised by regular arrays of α-keratin. Studies using synchrotron radiation have yielded not only the structure of α-keratin per se and that of the specific α-keratin in hair but have also revealed and identified the molecular changes that occur in human hair in insulin dependent diabetes.

It has now been surprisingly found that fibre x-ray diffraction studies using synchrotron radiation can reveal clear and consistent changes in the ultrastructure of hair from breast cancer patients.

According to a first aspect of the present invention, there is provided a method for detecting the presence of a gene responsible for a pathological state; or the pathological state itself in a patient comprising exposing at least one hair from the patient to fibre x-ray diffraction and detecting changes in the ultrastructure of the hair.

According to a second aspect of the present invention, there is provided an instrument for detecting the presence of a gene responsible for a pathological state; or the pathological state itself, using a hair sample, comprising: an X-ray source producing a beam of X-ray radiation; a sample stage for positioning said hair sample within said beam; a detector to detect the scattering of said X-ray beam caused by said hair sample; and a display means associated with said detector for displaying the output thereof; whereby patterns of output related to the presence of said gene or said pathological state are displayed for interpretation.

Suitably, the X-ray used are derived from synchrotron radiation or other monochromatic X-ray sources providing X-rays within the energy range of five to twenty-five keV.

In practice, a single hair is taken from adjacent to the scalp or other areas such as the pubic area of a person. The sample is washed in distilled water and dried under normal conditions (temperature 20° C. and atmospheric pressure), and then cut into approximately 30 mm lengths. The specimen is mounted in a cell, under sufficient tension to maintain alignment. The cell is then placed on a low-angle diffractometer so that the sample is normal to the beam. The space between the sample and the imaging plate is evacuated so as to minimise absorption losses and air scattering.

The X-ray diffraction experiments are carried out using a monochromatic X-ray source such as a low-angle synchrotron facility, for example at B115, Photon Factory, Tsukuba or the like with an X-ray wavelength ranging between 0.06 and 0.20 nm. An incident flux at the specimen of approximately $8 \times 10^{10}$ photons/sec can be generated when the Photon Factory storage ring is operated at 25 GeV with a beam current of 145 mA. A 0.15 nm wave-length was used at this facility. The X-ray patterns are recorded on imaging plates, for example Fuji Bas III imaging plates. Exposure time for the hair sample is suitably between 5 seconds and 5 minutes using synchrotron sources, but may be days or weeks using other X-ray sources. Preferably, the exposure time is approximately 60 seconds on second generation synchrotron sources and 20 seconds on third generation synchrotron sources. Sample to imaging plate distances are approximately 20 mm to 3000 mm. Suitably 400 mm is used. The analysis of the recorded patterns is carried out using two computer packages. The meridional data is analysed using a Bragg analysis, the equatorial data is analysed using appropriate Bessel functions.

BRIEF DESCRIPTION OF THE DRAWINGS

A number of embodiments of the present invention will now be described with reference to the drawings in which.

DETAILED DESCRIPTION

The following describes one embodiment of the invention which should not be construed as limiting on the scope thereof.

Figure 1:
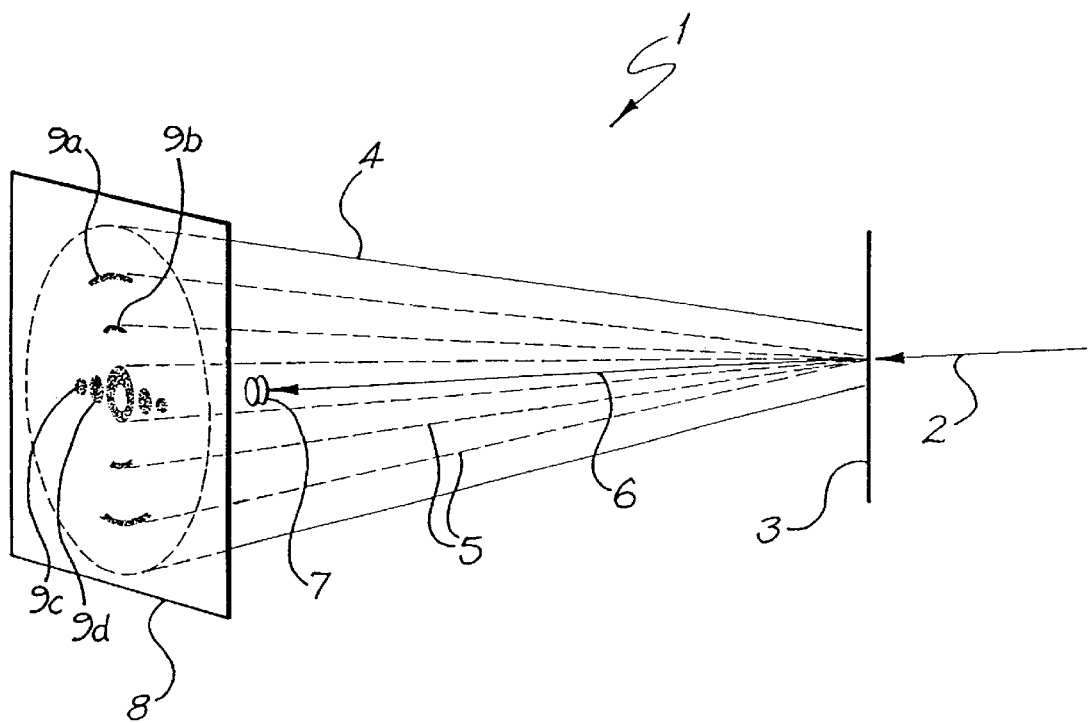
FIG. 1 is a schematic representation of the X-ray analysis system of this invention.

FIG. 1 depicts the system 1 for analysing hair according to the present invention. An X-ray source, represented schematically by the arrow 2 is a collimated monochromatic X-ray beam which irradiates a single strand of hair 3. Reference numeral 4 refers to what is known in the art as the "evacuated X-ray flight path". Within this flight path, the scattered X-rays 5 are deflected from the direction of the unscattered beam 6. The unscattered beam 6 is occluded by a beam stop 7 while the scattered X-rays arrive at imaging plate 8 and are detected as shown schematically by reference numerals 9a, 9b, 9c and 9d.

As mentioned above, the pattens appearing on the imaging plate may be analysed by methods well known in the art.

Figure 2:
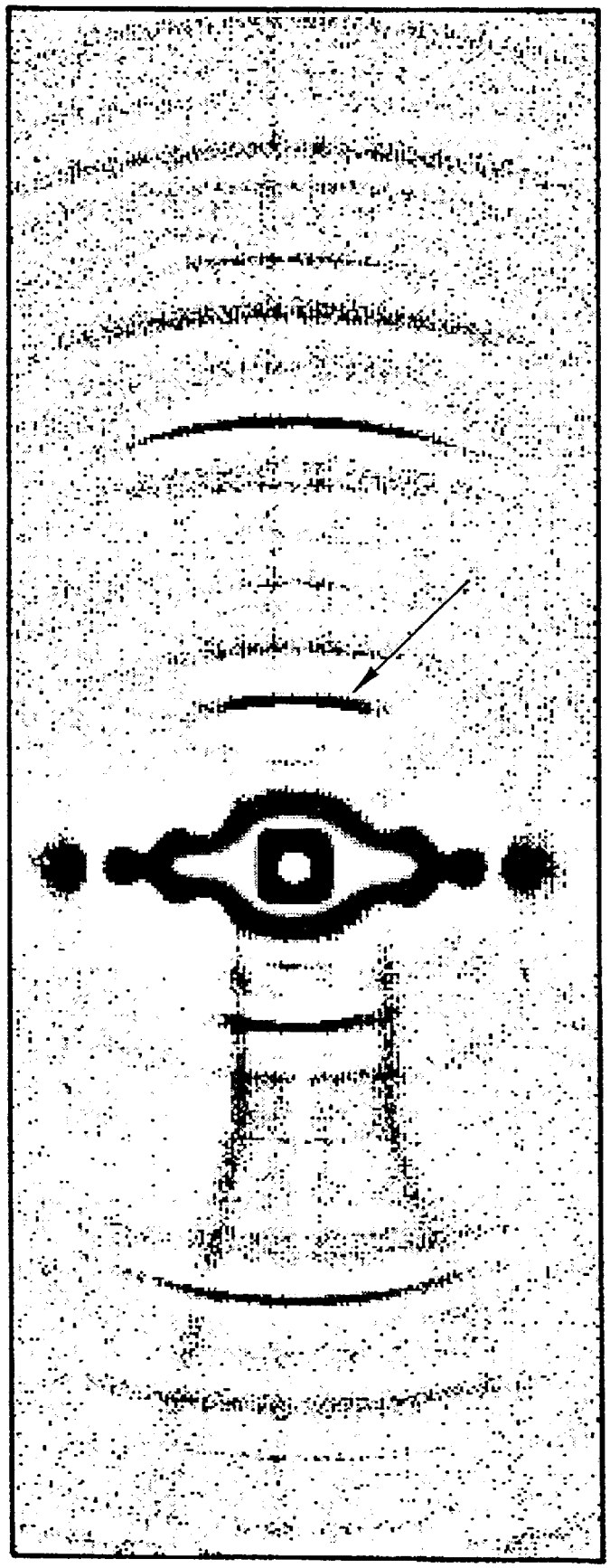
FIG. 2 is an x-ray diffraction pattern obtained from normal hair.

We have found that normal hair of all post-partum persons so examined yielded distinctive, repeatable patterns which varied only slightly over the age range from 4 years to 80 years. A typical pattern of normal hair is given in FIG. 2. This is a typical synchrotron x-ray diffraction pattern of human hair obtained for persons without breast cancer. The meridional reflections result from the arrangement of the helices along the axis of the fibre. The equatorial pattern results from the highly oriented cylindrical packaging of the α-keratin fibres in the cortex. The insert shows the central section of the pattern after background correction. The arc, indicated by the arrow, is the first order Bragg reflection, resulting from the plasma membrane which surrounds each cortical cell and is therefore perpendicular to the fibre.

A second set of hair samples included hair from:

(a) patients with breast cancer known to possess one or other familial gene.

Figure 3:
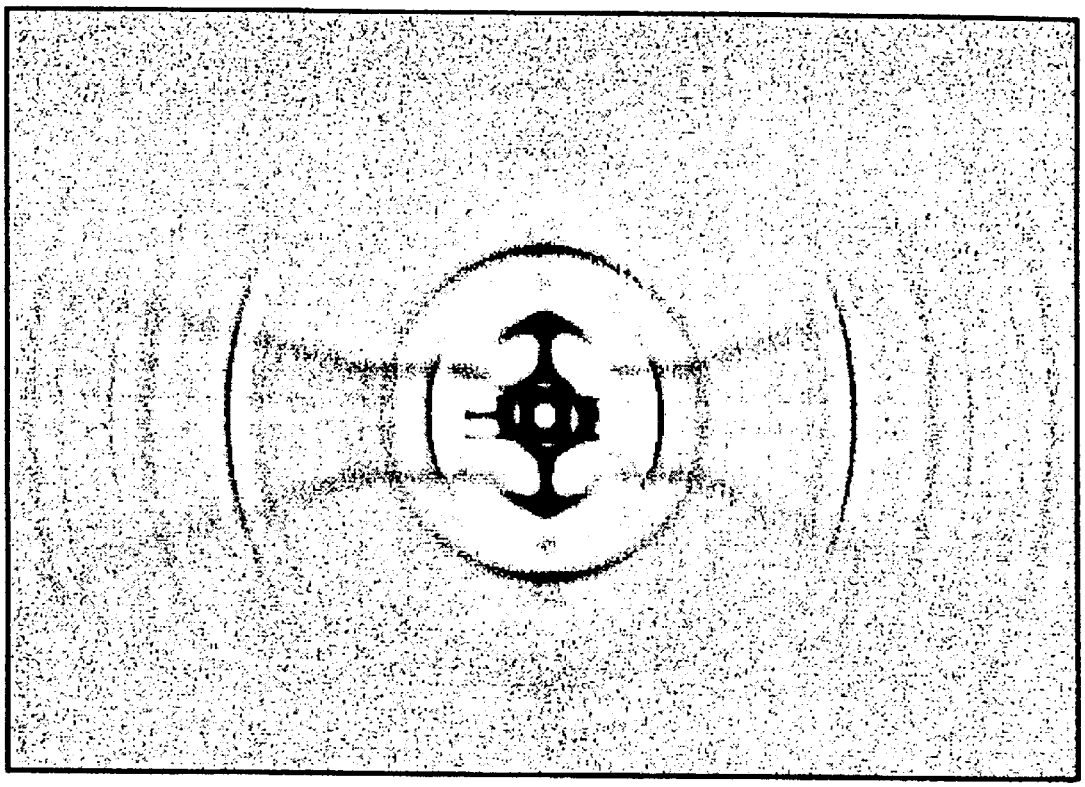
FIG. 3 is a typical x-ray diffraction pattern obtained from hair of patients with breast cancer.
Figure 4:
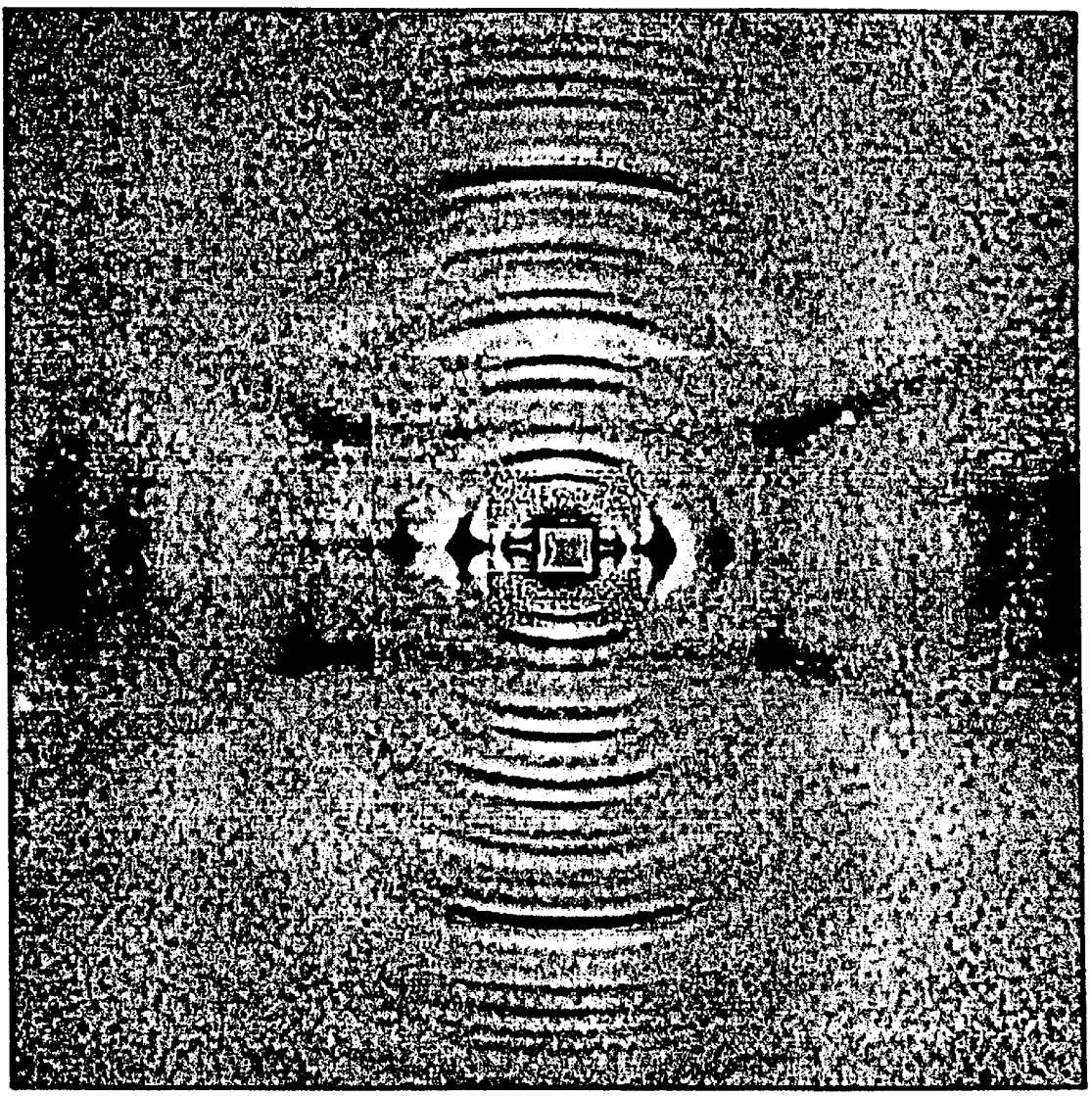
FIG. 4 is a further x-ray diffraction pattern from normal hair.
Figure 5:
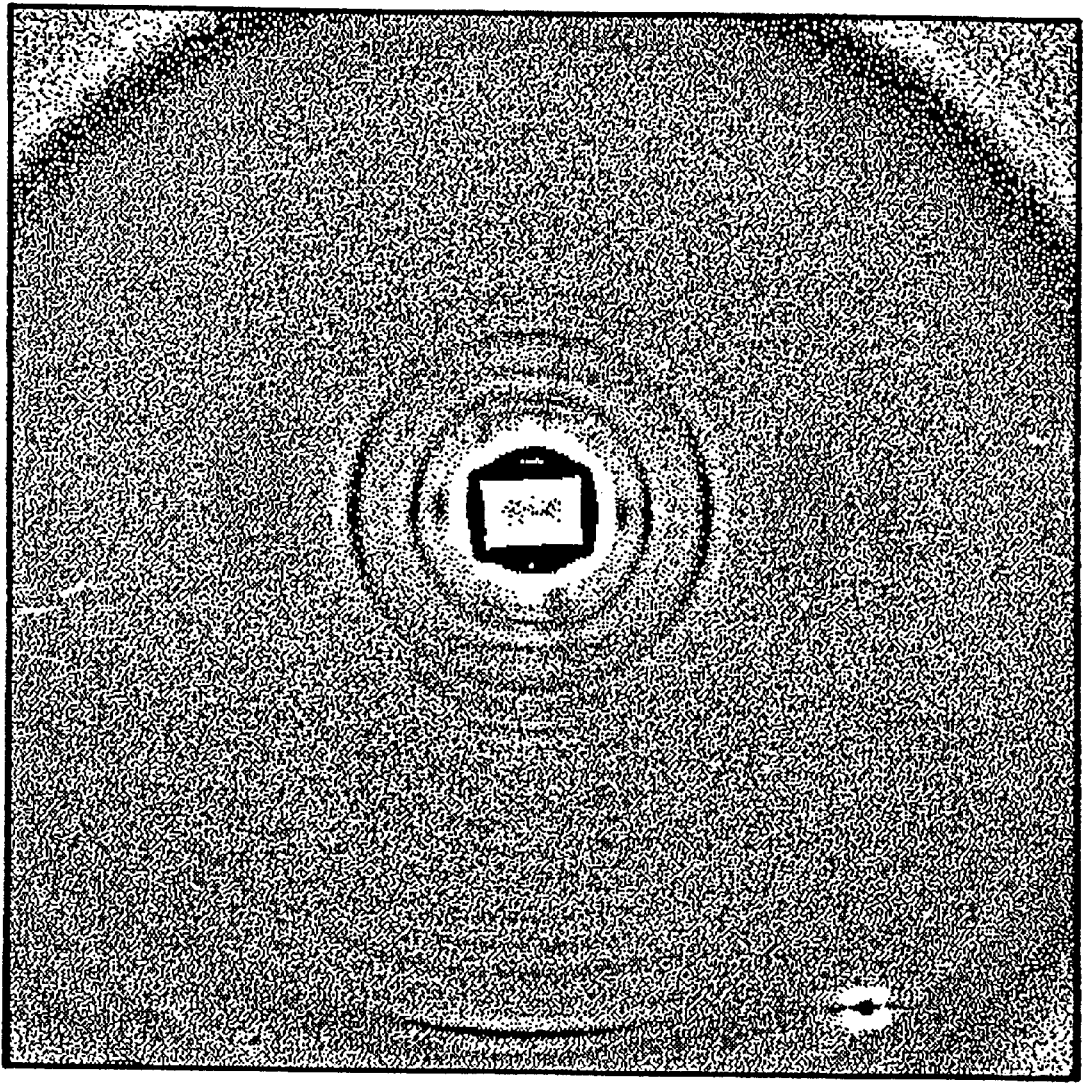
FIG. 5 is a further typical x-ray diffraction pattern obtained from patients with breast cancer.

(b) patients with breast cancer known to not possess either familial gene, (c) younger members of families with a history of breast cancer. These members have risks of about 1 in 4–5 of developing breast cancer. All such hair samples yielded changes in the synchrotron diffraction studies, a typical example of which is given in FIG. 3. This Figure is a typical synchrotron x-ray diffraction pattern of human hair from breast cancer patients. The ring structure is superimposed onto the diffraction pattern obtained for the controls. The insert shows the inner section after background correction and clearly demonstrates that the first order of the ring pattern corresponds to the same spacing as the first order Bragg reflection arising from the plasma membrane of the controls. The results indicate that the changes observed are related to breast cancer per se. In the case of family members, two members of one family showed a change, the third did not. This fact would indicate that carrying a breast cancer gene or genes may produce this abnormality and this technique can distinguish which members of the family actually have the abnormality.

The changes which we have observed were manifested by all samples of scalp and pubic hair taken from women with breast cancer and were also observed for persons who have tested positive to the familial BRCA genes but as yet have no cancer. In all such cases, the x-ray diffraction patterns for normal human hair are superimposed by a ring or set of rings which corresponds to a spacing of 4.44±0.06 nm. The nature and position of this powder pattern indicates that extra material is bound in a completely random array onto the cell membrane complex during formation of the fibre in the follicle. The reproducibility of these changes indicates that similar hair analyses as those described here should be suitable for a simple non-invasive detection of breast cancer at an early stage.

The invention is further illustrated by way of the following examples which again, are not to be construed as limiting on the scope of the invention thereof

EXAMPLE 1—SCALP HAIR

Double Blind Pilot Study (Japan)

The first double blind pilot study carried out on Beamline 15A at the Photon Factory (Japan) revealed an additional ring or rings in the x-ray diffraction patterns for some samples. After correlating the samples with known patient data, it was proposed that the changes might indicate a propensity to malignancy and be related to breast cancer per se.

EXAMPLE 2—SCALP HAIR

Clinical Trial (Manchester, UK)

To investigate the observation made in Example 1, a larger clinical trial set was provided by Christie CRC Research Centre (Manchester, UK) for a further double blind experiment. This was carried out on the Australian National Beamline Facility at the Photon Factory (Japan) and the results verified at higher resolution on the BIOCAT Beamline at the Advanced Photon Source (Chicago, USA). The results initially showed some ambiguity.

EXAMPLE 3—SCALP HAIR

Further Investigation

The ambiguity demonstrated in Example 2 was investigated where it was shown that permanent setting treatments were the cause of the problem. Such hair treatments invariably lead to the breakdown and remaking of covalent bonds producing structural irrevocability. A subset of the original large set was obtained wherein any samples from persons who had had such hair treatments over the last three months were removed.

EXAMPLE 4

X-ray Diffraction Studies of Pubic Hair (Sydney, Australia)

In order to obviate the problems demonstrated in Example 3, a set of pubic hair was supplied by the Oncology Unit, St George Hospital (Sydney, Australia). For the experiment, single and multiple strands of hair were washed in distilled water, dried and placed in specially constructed cells to hold them taut in and normal to the x-ray beam. At all facilities the x-ray scattering patterns were recorded using Fuji-BAS imaging plates. The irradiation wavelengths varied from 1 to 1.5 A with camera lengths ranging from 400 to 2400 mm. Exposure times varied from 10 seconds to 10 minutes depending on the synchrotron source and the x-ray optical configuration.

Analysis of data from each facility showed that the patterns were consistent and revealed that the structure of the $\alpha$-keratin fibrils does not change. The meridional reflections for all samples correspond to the expected infinite lattices of 47.0 nm and 62.6 nm. The packing parameters were obtained from a full Bessel function analysis of the equatorial maxima and were consistent for all samples. These values gave the radius for the $\alpha$-keratin helix as 0.92±0.02 nm, the radius of the tetramer as 2.1±0.3 nm, the radius of the IF as 3.71±0.09 nm and the centre to centre spacing of the IFs as 0.3±0.05 times the radius of the IF.

The rings that characterise the breast cancer tissue correspond to a spacing of 4.44±0.06 mn which places them directly in the position of the equatorial are representing the plasma membrane in the normal hair pattern. The ring signifies that the membrane has suffered some wrinkling or disordering of its orientation, possibly due to the binding of some material to the membrane's outer layer. Further studies are underway to determine what the nature and position of this extra material might be.

EXAMPLE 5

Summary of Results of Scalp Hair and Pubic Hair

All of the 8 samples of pubic hair and all of the 15 samples of scalp hair from patients with breast cancer showed the change whilst all of the 4 samples of pubic hair and 13 out of the 16 samples of scalp hair from the normal controls did not show the changes. A further set of scalp hair samples were taken from a group of persons who had a family history of breast cancer and who had therefore been tested for the BRCA genes at the Cancer Clinics attached to the Withington and Christie Hospitals, Manchester. Of those known to have tested positive to the BRCA genes but as yet unaffected, 3 out of 5 showed the clear change and the remaining 2 out of 5 showed a diffuse ring in the same position indicating partial change. Only 1 out of 8 of those that had tested negative to the gene showed a change the remainder were normal. None of the pubic hair samples came from patients with a family history of breast cancer.

EXAMPLE 6—SCALP AND PUBIC HAIR

Further investigation (Portland, Oreg.)

This was a set of 19 samples obtained from Eastmoreland Hospital, Portland. Oreg. Only one of these patients had a very strong familial history of breast cancer, but as yet no diagnosable cancer. This patient was correctly identified. The chance of correctly identifying this person and only this person is approximately 1 in 500,000. These samples were studied at Beamline Facility (Photon Factory, Japan) and checked on Beamline 15A at the Photon Factory (Japan).

EXAMPLE 7

Knock-out Mice Confirmatory Study

Figure 6:
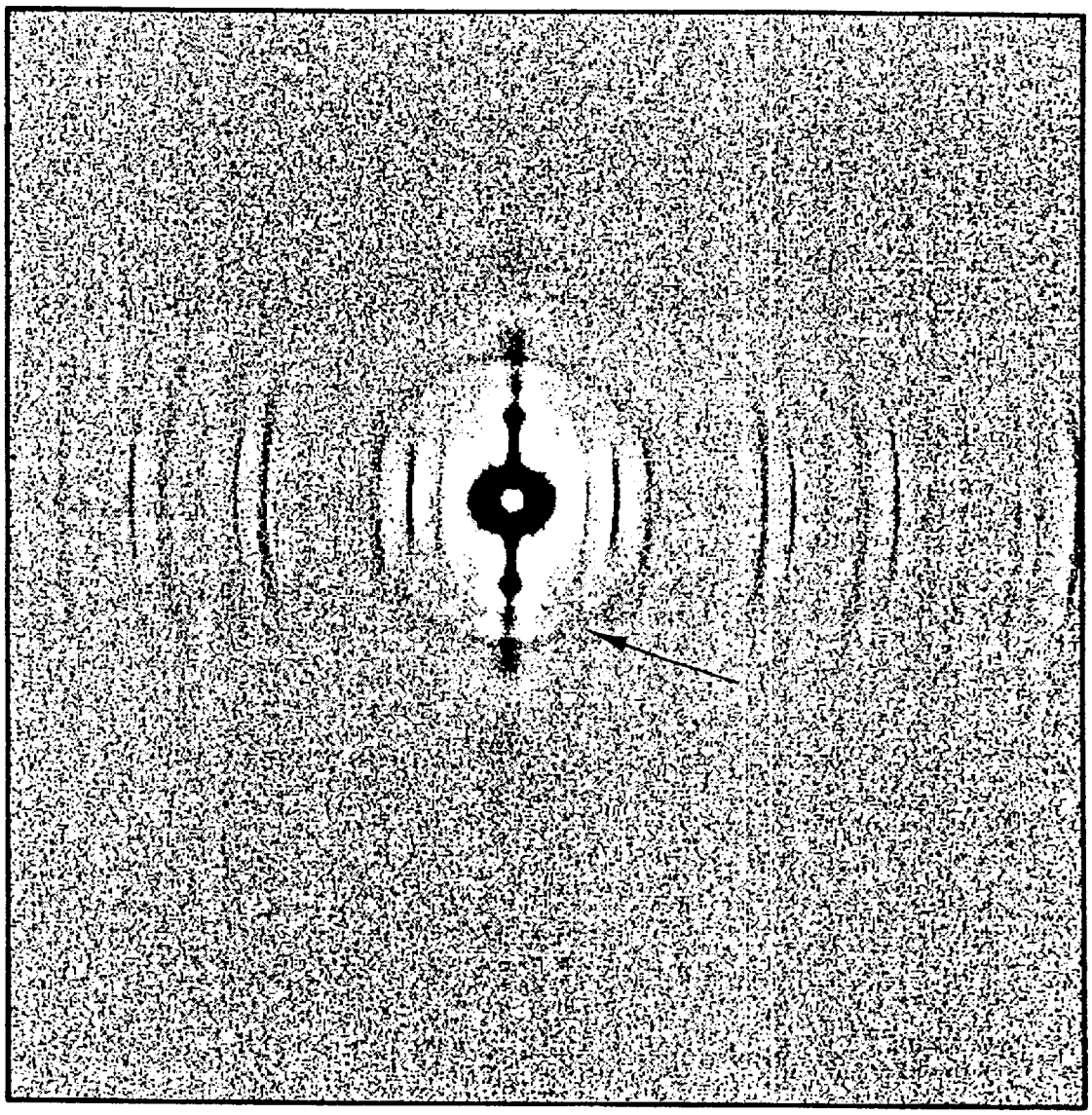
FIG. 6 is an x-ray diffraction pattern obtained from hair from BRCA1 knock-out mice showing a very weak ring (indicated by an arrow)

The particular change associated with the BRCA1 gene and observed in the above case has been confirmed in a separate study of transgenic mice. The BRCA1 knockout mice, (heterozygotes), were obtained from the Molecular Pathogenesis Section, National Human Genome Research Institute, National Institute of Health, Bethesda, Maryland The six BRCA1 knockout mice all showed the weak ring in FIG. 6. This ring was not seen in any of the 6 normal mice.

EXAMPLE 8—PUBIC HAIR

Further Investigation (Sydney, Australia)

In addition to this we have been able to isolate correctly a subset of 21 out of 22 breast cancer patients in a mixed set of 150 samples obtained from the Oncology Unit, St George Hospital (Sydney, Australia).

A person who was not identified in this set has been in remission for more than five years and the oncologists believe that she might be completely clear. A person in similar circumstances had been shown to be clear in our first study and a further eight such cases have been cited in our most recent study.

EXAMPLE 9

Prostate Cancer

Figure 7:
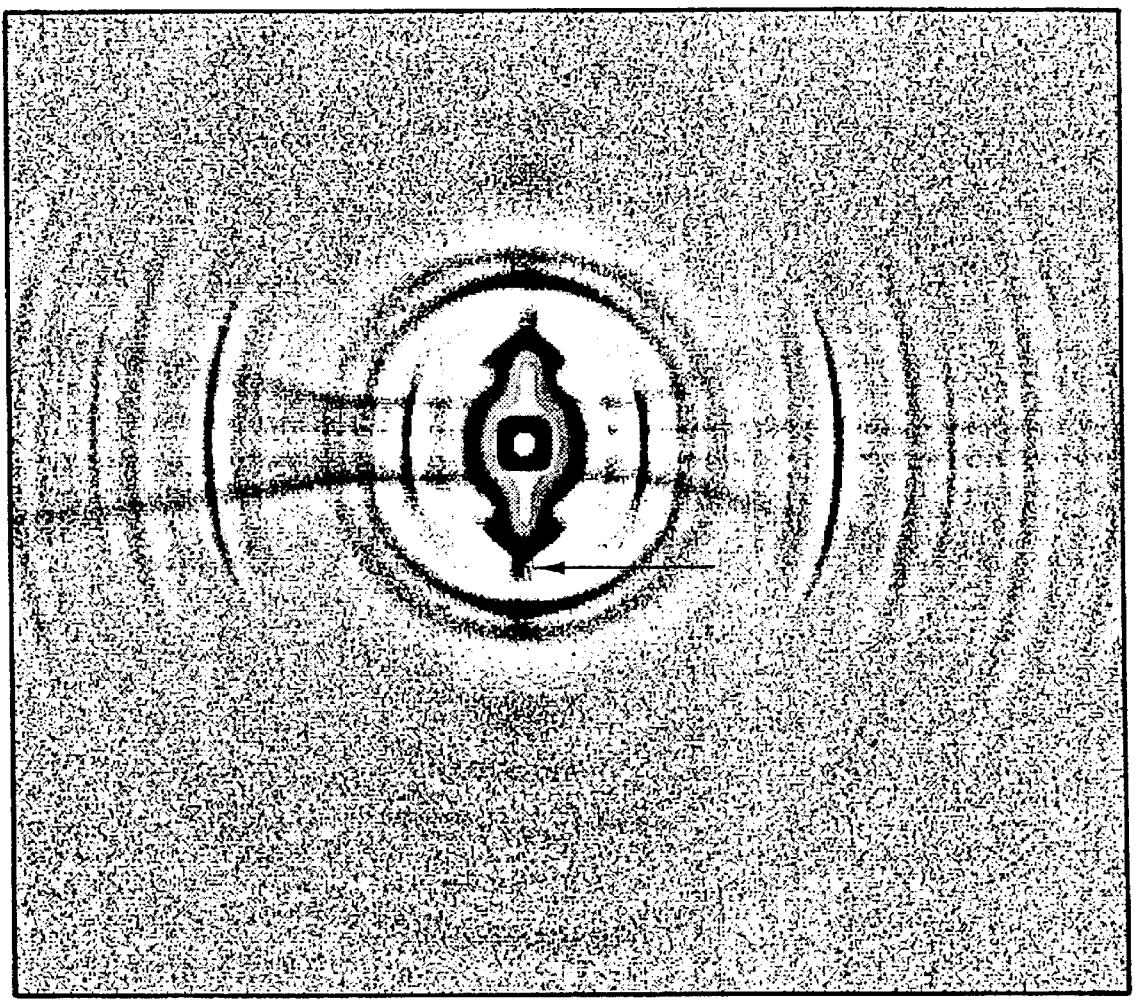
FIG. 7 is an x-ray diffraction pattern from hair of a person with prostate cancer showing an extra reflection (illustrated by an arrow on the Figure)

A further subset of 20 of the above-mentioned 150 samples were from men with prostrate cancer and were correctly isolated. These men ranged in age from 50 to 90. FIG. 7 indicates the pattern obtained for each of these males.

EXAMPLE 10

Alzheimer's Disease (Perth, Australia)

Figure 8:
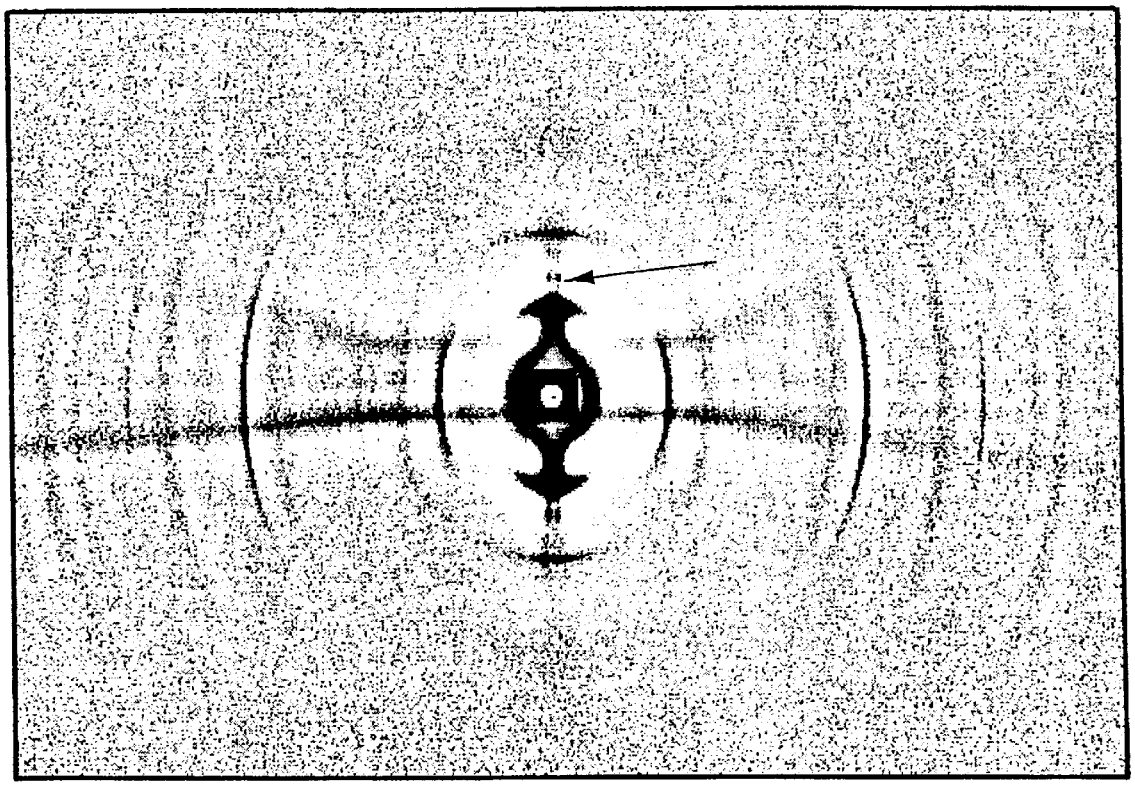
FIG. 8 an x-ray diffraction pattern from hair of a person with Alzheimer's disease showing an extra reflection (illustrated by an arrow on the Figure)
Figure 9:
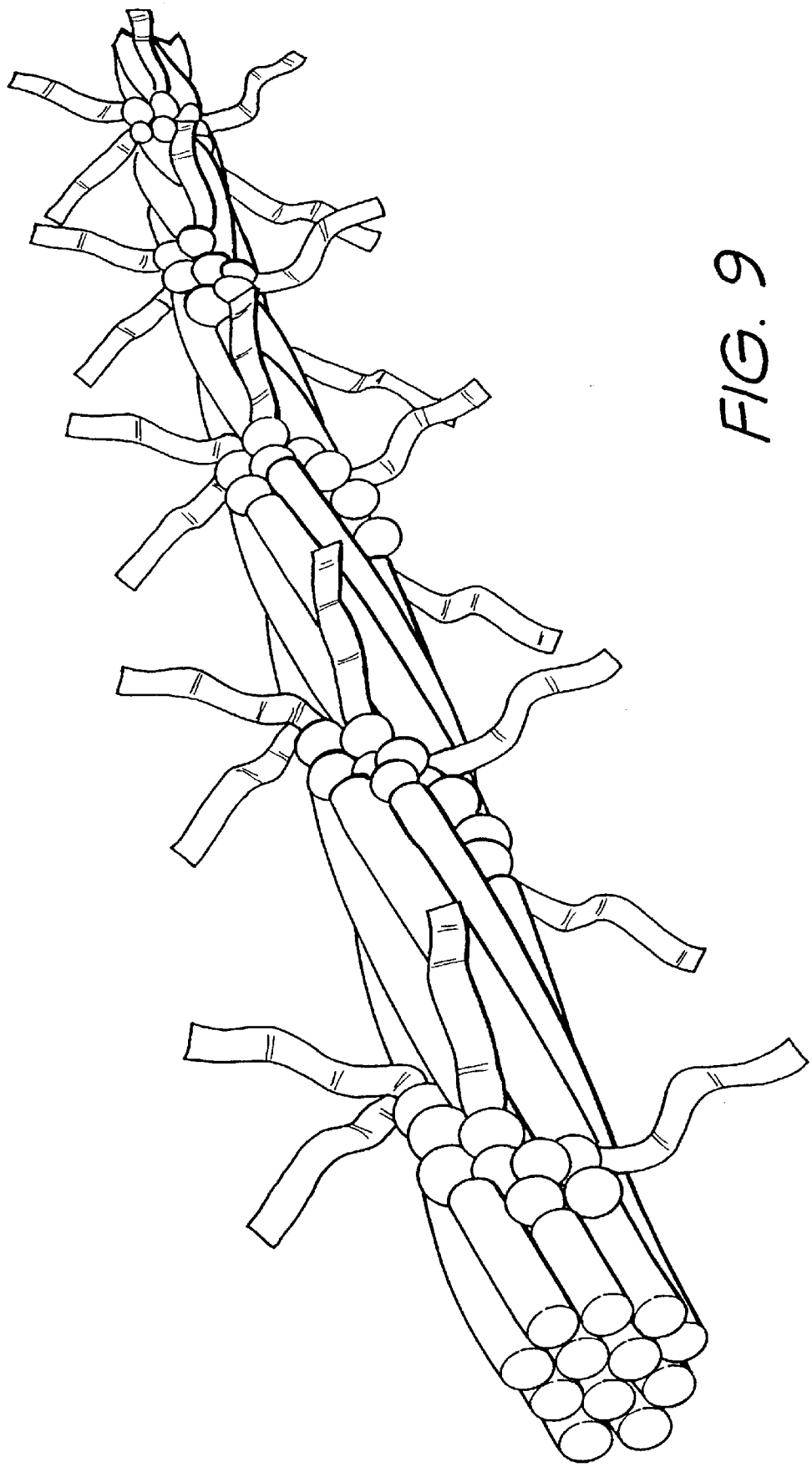
FIG. 9 is an illustration of the helical arrangement of tetramers in the hair of a normal mouse.

All 25 patients with Alzheimer's Disease were correctly identified from a set of 50 samples of hair from the Department of Surgery, The University of Western Australia, Perth. The ages of those diagnosed as having Alzheimer's Disease ranged between 44 and 93. The pattern which identifies Alzheimer Disease is given in FIG. 8. The pattern of spots seen in the equatorial directions would suggest a crystalline material bound to the tetramers normally arranged as in FIG. 9, thus pushing them apart. One sample which was marked on the code kept in Perth as having Alzheimer's Disease at the time of collection, March 1999, appeared as normal on my results. When checks were carried out at the special Alzheimer's Nursing Home for correlation of the stage of the disease with the degree of change observed it was revealed that the initial diagnosis for this person had been changed mid-year.

Discussion

Although the number of samples investigated so far is in total over 400, the reproductibility of the results is most encouraging. The flexibility of this technique and the fact that using synchrotron sources each sample takes seconds to measure and only minutes to interpret makes its possible use as a rapid and accurate diagnostic tool for breast cancer, prostate cancer, and Alzheimer's disease.

It should be clear that the present invention will find wide applicability in the medical field, particularly in the area devoted to detecting the propensity of a subject to breast cancer, prostate cancer, and Alzheimer's disease.

What is claimed is:

1. A method for detecting the presence in a patient of a gene responsible for a pathological state or the pathological state itself, said method comprising exposing at least one hair from the patient to fiber x-ray diffraction and detecting changes in ultrastructure of the hair that indicate the presence in the patient of the gene or the pathological state, said pathological state being (a) a cancer that causes a change in the ultra structure of the hair or (b) Alzheimer's disease.

2. The method according to claim 1, wherein the pathological state is breast cancer.

3. The method according to claim 2, wherein the hair is taken from a scalp or pubic area of the patient.

4. The method according to claim 2, wherein the hair is washed in distilled water and dried prior to said exposing.

5. The method according to claim 2, wherein the x-ray diffraction is carried out with a low-angle synchrotron facility.

6. The method according to claim 2, wherein the x-ray diffraction is carried out with x-rays having a wavelength of about 0.15 mm.

7. The method according to claim 2, wherein the hair is exposed to x-rays for a period of between 5 seconds and 5 minutes.

8. The method according to claim 7, wherein the exposure time is approximately 60 seconds.

9. The method according to claim 1, wherein the pathological state is prostate cancer or Alzheimer's disease.

10. The method according to claim 9, wherein the x-ray diffraction uses x-rays from synchrotron radiation or other monochromatic x-ray sources with energies between 5 and 25 keV.

11. The method according to claim 10, wherein monochromatic x-rays are used that have a wavelength between 0.06 and 0.20 nm.

12. The method according to claim 9, wherein synchrotron radiation is used from a low-angle synchrotron facility.

13. The method according to claim wherein the hair is taken from a scalp or pubic area of the patient.

14. The method according to claim 9, wherein the hair is washed in distilled water, dried and positioned perpendicular to a beam and held taut during said exposing.

15. The method according to claim 9, wherein the hair is exposed to x-rays from third or second generation synchrotrons for a period of approximately 20 or 60 seconds respectively.

16. The method according to claim 9, wherein the hair is exposed to x-rays for a period of between about 5 seconds to about 5 weeks.

17. The method according to claim 9, wherein the pathological state is prostate cancer.

18. The method according to claim 9, wherein the pathological state is Alzheimer's disease.

* * * * *